United States Patent [19]

Farley

[11] 3,994,283

[45] Nov. 30, 1976

[54] GLOW PATTERN VIEWING CELL AND APPARATUS FOR LIVING ORGANISMS

[76] Inventor: Glenn R. Farley, 3024 Verano Pl., Irvine, Calif. 92715

[22] Filed: May 14, 1975

[21] Appl. No.: 577,542

[52] U.S. Cl. .......... 128/2 A; 128/DIG. 15
[51] Int. Cl.[2] .......... A61B 6/00
[58] Field of Search .......... 128/2 R, 2 A; 350/160 R; 354/62

[56] References Cited

UNITED STATES PATENTS 3,257,903 6/1966 Marks .......... 350/160 R UX

OTHER PUBLICATIONS

The Sciences, "Pictures of an Unknown Aura" by Steve Aaronson, pp. 15–22.

*Primary Examiner*—Anton O. Oechsle
*Attorney, Agent, or Firm*—Ancel W. Lewis, Jr.

[57] ABSTRACT

In glow pattern viewing apparatus for observing glow patterns surrounding living organisms there is provided a viewing cell having a pair of opposed outer layers of transparent dielectric material separated by a transparent sheet of electrolyte to which an electric voltage is applied. The placement of a living organism on one of the outer layers with the electrolyte activated produces an electric field between the electrolyte and the organism through the outer dielectric layer against which the organism is placed causing a visible glow pattern about the organism that is observed by looking through the viewing cell, the glow pattern characterizing the condition of said living organism. A loop of conductive wire in electrical contact with and around the periphery of the sheet of electrolyte conducts electric energy from a power supply to the electrolyte. In one form a housing contains the viewing cell and power supply and is provided with a viewing opening and an access opening, these openings preferably being covered with opaque cover members that inhibit light about the viewing cell for clearer observations of the glow pattern. In another form the viewing cell is pivotally mounted to swing to a selected orientation about a fixed axis. The power supply activating the electrolytic layer provides high frequency, high voltage, low current, electric pulses that are adjustable in amplitude and frequency.

21 Claims, 14 Drawing Figures

GLOW PATTERN VIEWING CELL AND APPARATUS FOR LIVING ORGANISMS

This invention relates generally to viewing apparatus and more particularly to a novel viewing apparatus for use in observing glow patterns about living organisms.

As background, it has been recognized that changes in the course of the life processes are accompanied by changes in the dielectric structure and or electrical characteristics of living organisms. Accordingly, living organism exhibit a continual change in electrical qualities or conditions. It has been observed that functioning muscles and nerves of a living body generate electrical activity that can be monitored by attaching electrodes to the living body. A number of devices have been devised for monitoring electrical activity within a living body such as the EKG, EEG and EMG. Other devices have been developed to monitor radiated electric fields or electric radiation and measure the biological voltages in a human body.

While the precise nature and quality of the electrical character or condition of a living organism, plant, animal or human has been the subject of considerable study, a considerable amount is yet to be fully understood. A living organism has been found to exhibit a certain glow pattern when at substantially ground potential and positioned on a dielectric layer adjacent a conductive plate to which electric energy is applied. This glow pattern is photographed in the practice of what is commonly referred to as Kirlian photography in which a photographic film is placed between an electrically activated plate and the living organism and a glow pattern appears about the living organism on the film when the film is developed. These glow or aura patterns or images exhibit a wide variation in brightness, color, size and character. For example, a healthy leaf exhibits a considerably different glow pattern than a wilted leaf and a healthy person exhibits a considerably different glow pattern than an ill person, leaving open the possibility of diagnostic value in medicine for the detection of diseases or the like by study of these glow patterns which have sometimes been referred to as the aura. It is quite likely that such factors as organism health and moods can be analyzed by studying these glow patterns.

A disadvantage of the photographic technique practiced by Kirlian is that it gives the condition only at one instant and a number of timed photographs are required to give conditions at various time intervals.

Accordingly, it is an object of the present invention to provide a viewing apparatus that displays a glow pattern or aura of a living organism on a continuous or on-going basis.

Another object of the present invention is to provide a novel glow pattern viewing cell for living organisms characterized by its transparency whereby a viewer can look through the viewing cell to view directly the glow pattern of an object placed against the cell with the alternative of directly photographing the glow pattern on the viewing cell if desired.

Still a further object of this invention is to provide a novel and improved viewing apparatus characterized by a relatively simple electric circuit providing a range of electrical voltages and frequencies and having considerable adjustability for different living organisms.

Still a further object of the present invention is to provide a novel sandwich type transparent viewing cell that is relatively simple and inexpensive to manufacture and is highly effective in displaying glow patterns of living organisms.

Another object of this invention is to provide a relatively portable viewing apparatus in which the area around the glow pattern can be maintained dark by use of an opaque cover member.

Other objects, advantages and capabilities of the present invention will become more apparent as the description proceeds taken in conjunction with the accompanying drawings, in which.

Figure 1:
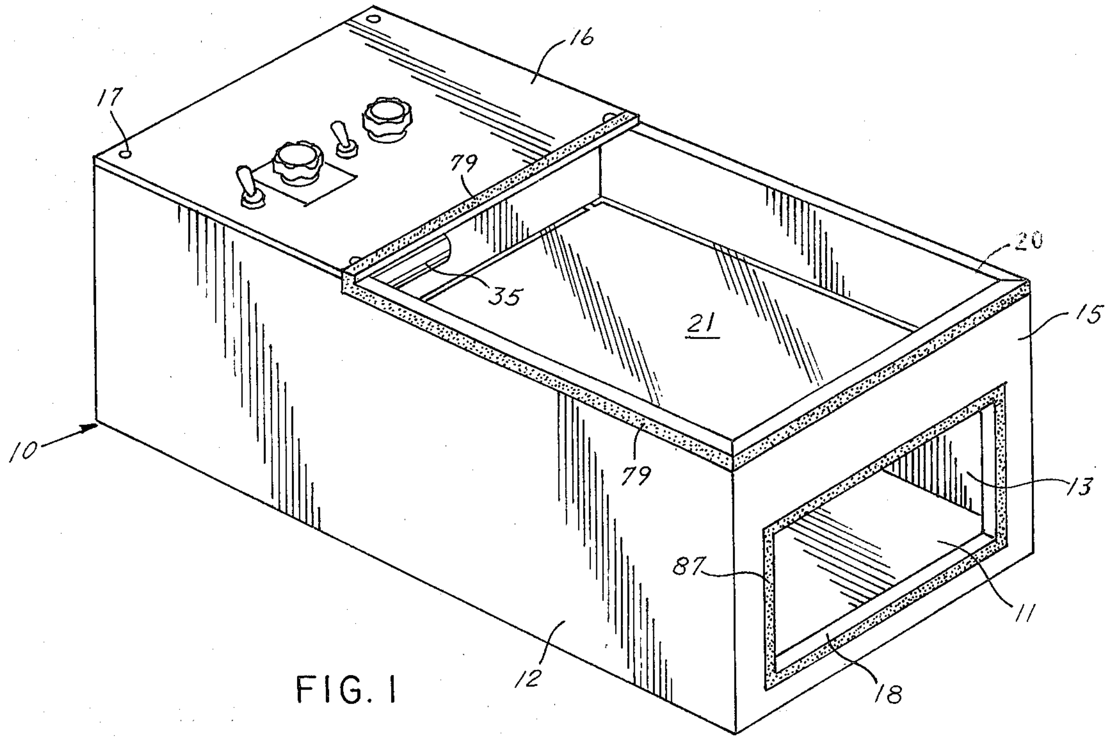
FIG. 1 is a top perspective view of viewing apparatus embodying features of the present invention with opaque cover members removed.

Referring now to the drawings, in FIGS. 1 through 6 there is shown viewing apparatus comprising a housing 10 disposed in a horizontal position and in this position is shown to have a bottom wall 11, a pair of spaced opposed side walls 12 and 13, opposed end walls 14 and 15 together with a removable cover 16 covering only a portion of the top of the housing leaving a viewing opening in the housing as described hereinafter. The top cover 16 forms a compartment for housing the electrical circuitry of the electric power supply described hereinafter. Top cover 16 is shown as releasably fastened at each corner by screws 17. End wall 15 has an access opening 18 which allows an organism, such as the human hand 19 being viewed, to be inserted into the housing.

Figure 2:
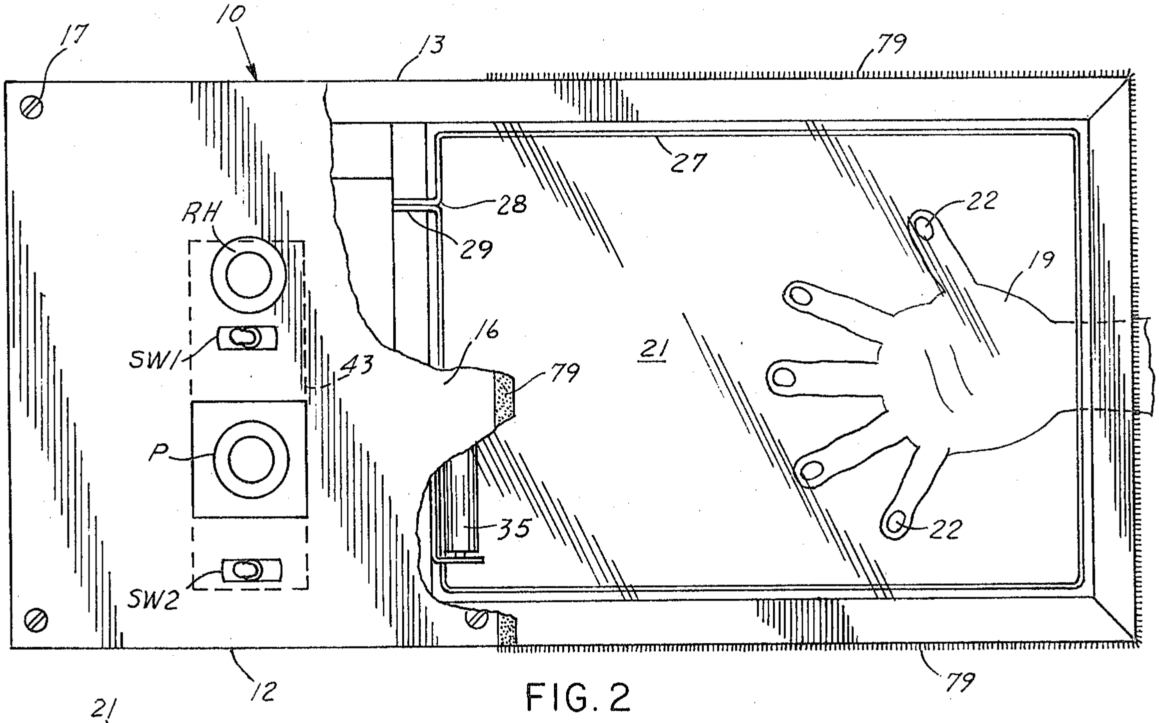
FIG. 2 is a top plan view of the viewing device of FIG. 1 with the outline of a hand shown therein with fingertips placed against the underside of the viewing cell.

While the device as shown in FIGS. 1 and 2 is on a horizontal supporting surface with the orientation of the walls being described with reference thereto, it is understood that this form may be readily wall-mounted with bottom wall 11 in a vertical position and attached to the supporting wall with end wall 15 then becoming the bottom wall.

A viewing cell 21 is mounted in a recessed or inwardly inset position from a viewing opening 20 in the top of the housing 10, the cell 21 being arranged parallel to top cover 16 and above access opening 18. The cell 21 is positioned in slots or recesses in the side walls 12 and 13. The hand 19 is shown with the palm facing up and with portions of the fingers or fingerprint area 22 of each finger of hand 19 pressed against the underside of the cell 21 for purposes of illustration.

Figure 3:
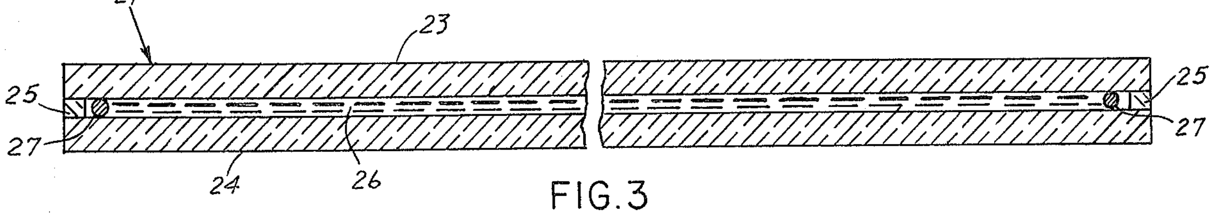
FIG. 3 is a fragmentary vertical sectional view through the viewing cell shown in FIGS. 1 and 2.

The viewing cell 21 shown in more detail in FIG. 3 is of a sandwich type structure comprised of a pair of opposed rigid outer layers or sheets 23 and 24 of a transparent, dielectric material separated by a relatively thin, narrow, rigid spacer strips 25 of the same material as layers 23 and 24 that extend along the edge or periphery of layers 23 and 24 throughout the peripheral extent thereof to hold the outer layers apart a selected distance with the space between layers 23 and 24 being filled with a transparent liquid electrolyte 26 which takes the form of a sheet. In the preferred form shown the outer layers 23 and 24 and spacer 25 are made of Plexiglas and the electrolyte is a relatively weak solution of salt water.

A loop of electrically conductive wire 27 extends between the outer layers adjacent and inwardly thereof just inside strip 25 and has end portions 28 that project through the cell to which is connected a common line 29 which in turn is connected to the output of the electric power supply described hereinafter. The loop 27 serves as an input means to connect the electric energy from the power supply to the electrolyte 26. The spacer strips are secured in place with a suitable adhesive at abutting edges to seal the electrolyte 26 between the outer layers 23 and 24.

Figure 4:
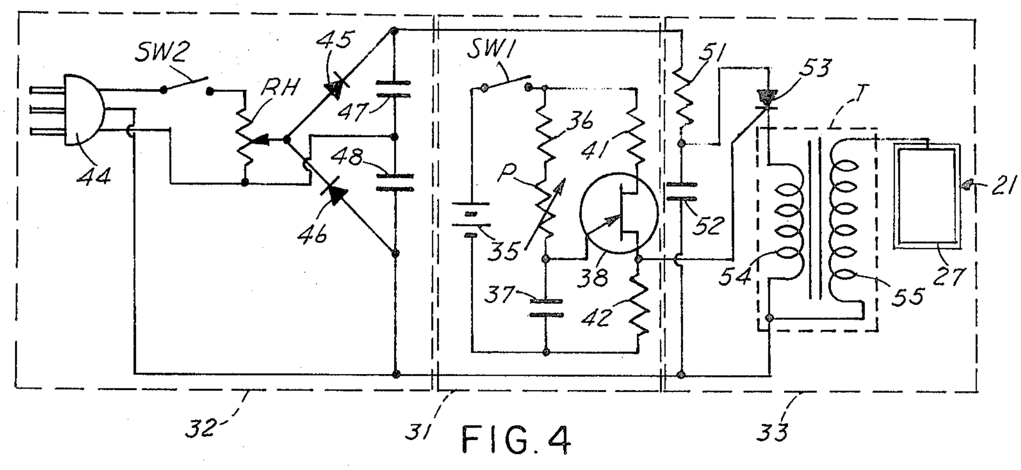
FIG. 4 is an electric circuit diagram of an electrical power supply in the apparatus of FIGS. 1 through 3.

An electric power supply for the viewing apparatus is shown diagrammatically in FIG. 4 and broadly has three parts, each part being encircled shown in dashed blocks designated 31, 32 and 33. Circuit 31 is an electric oscillator which comprises a battery 35 that supplies a DC voltage that is switched on and off to the rest of the circuit by a normally open switch SW1 In circuit 31, a resistor 36, adjustable potentiometer P and capacitor 37 are connected in series with one another across the battery 35 through switch SW1. Two electrodes of a unipolar junction transistor 38 are connected between resistors 41 and 42 in a series circuit across battery 35 through switch SW1 placing them in parallel with the series circuit of containing elements 36, P and 37. A gate electrode of the transistor 38 is connected between capacitor 37 and potentiometer P. Resistors 41 and 42 serve to bias the transistor 38 so that when the voltage appearing at its gate electrode reaches a certain limit, the transistor turns on or conducts via the other two electrodes associated with resistors 41 and 42 and puts out a current pulse that is used to control circuit 33 described hereinafter. Resistor 36 and potentiometer P provide a resistance through which the capacitor 37 is charged and the time of charging and thereby the frequency of the pulses used from circuit 31 is varied by changing the setting of the potentiometer P. Potentiometer P and switch SW1 of circuit 31 are shown as mounted on cover 16 to make them accessible to the operator from the top of cover 16. A common ground strip 43 is provided under the cover 16 for grounding switches SW1 and SW2, rheostat RH and potentiometer P for safety purposes.

Circuit 32 functions as an AC to DC converter and as shown is comprised of a switch SW2 and an adjustable rheostat RH connected across an AC input line (not shown) that is connected to a socket 44. A three-pronged socket 44 is shown to provide a ground. A selected portion of the AC voltage from the AC input line is applied to a voltage doubler configuration comprised of two diodes 45 and 46 connected back to back and two capacitors 47 and 48 connected across the diodes. This doubler configuration doubles as an AC voltage input and delivers a substantially DC voltage output across the opposite terminals of two capacitors 47 and 48. A change in the setting of the resistor RH will change the amplitude of the pulses or oscillations in the output circuit 33 described hereinafter.

Circuit 33 functions as the pulse output circuit and includes a resistor 51 and a capacitor 52 connected in series with one another in turn are connected across the capacitors 47 and 48 or output of circuit 32. Two electrodes of a silicon controlled rectifier 53 are connected in series with a primary winding 54 of a suitable pulse transformer T with this series circuit being connected between resistor 51 and capacitor 52. The pulse transformer may take various forms such as the form of a coil used in an auto ignition. The triggering electrode of rectifier 53 is connected to one of the electrodes of transistor 38 common to resistor 42 or the output of oscillator circuit 31. The rectifier 53 responds to the pulse produced by the circuit 31 and is turned on allowing current to alternately flow and turn off. The rectifier 53 then acts somewhat like a switch when it receives a current pulse and turns on and allows current to flow and turns off in an alternating cycle. The rectifier 53 turns off when the current falls below a certain level and at which time the rectifier withstands voltages preventing current flow until it receives another current pulse from circuit 31. The resistor 51 provides a path for current to flow from the power supply circuit 32 allowing the capacitor 52 to charge when the SCR is turned off. Secondly, resistor 42 limits the current that can flow from the power supply circuit 31 in conjunction with the primary winding 54 and allows the current level to fall enough to turn the rectifier 53 off once it has turned on. The capacitor 52 charges during the off cycle of the rectifier 53 reaching a given positive voltage. When the rectifier 53 is then turned on it discharges through the SCR and the primary winding 54 providing a transient voltage and current flow through the primary winding 54. The transformer has a secondary output winding 55 that steps up the voltage and steps down the current so a high voltage low current transient wave as represented at 57 in FIG. 5 appears at the secondary winding 55. The opposition of the coil to a sudden current flowing through it causes a negative high voltage, low current transient wave represented at 58 in FIG. 5. Accordingly, at the output of the transformer there is shown a positive pulse designated 57 followed by a negative pulse designated 58 represented in FIG. 5 and this is continuous and repetitive in that the same wave form repeats each cycle. Moreover, this wave form is alternating or oscillatory in that it goes positive and then negative in relation to a reference time line.

The above power circuit affords variations in the voltage, current, frequency and waveform shape to afford the most effective glow pattern about the living organism. The voltage required must be strong enough to enhance electric discharges from the organism being viewed. It is estimated that a voltage of several thousand volts (peak-to-peak) would be sufficient and a circuit of the type described herein has the capability of producing voltages as high as about 1,000,000 volts peak-to-peak. The current levels are minimized to avoid possible tissue damage and are in the micro-amp range on the order of 1 micro-amp and below. The frequency of the pulses or oscillations as above noted is varied by changing the setting of the potentiometer P. An approximate frequency range for this circuit is between 0.5 and 5000 pulses per second.

Figure 9:
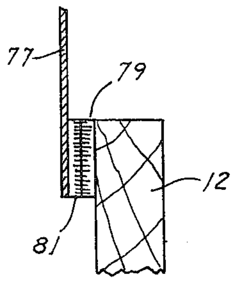
FIG. 9 is a fragment showing the attachment of the top cover member to the housing.
Figure 10:
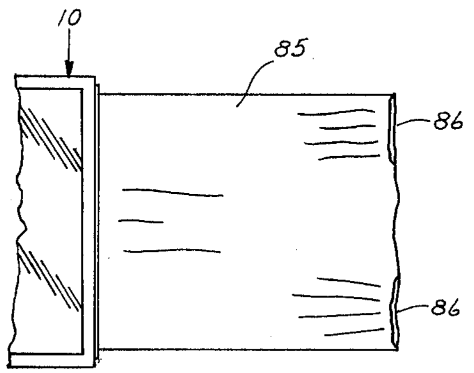
FIG. 10 is a top plan view of the end cover member.

For obtaining better viewing in daylight, a cover member 77 for the viewing opening 20 is mounted on the top of the housing 10. The cover member 77 is held by a suitable frame 78 removably supported on the edges of walls 12, 13 and 15 and cover 16 and cover member 77 to maintain the area around the viewing cell 21 dark. This cover member 77 has an opaque, flexible portion made of a dark, flexible fabric material and has an open end. At the upper end of the flexible fabric portion of member 77 there is provided a viewing head 82 with a lens 83, the viewing head 82 being conformable to the eyes of the viewer so as to be able to look down into the cover member 77 and view the images on cell 21. The open end of cover member 77 is releasably attached at the viewing opening 20 to the housing by the provision of a velcro-type strip 79 on the housing about opening 20 and a complementary velcro-type strip 81 on the cover member 77 at the open end as best seen in FIG. 9.

Figure 11:
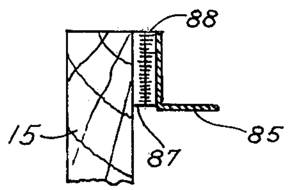
FIG. 11 is a fragment showing the attachment of the end cover member to the housing.
Figure 12:
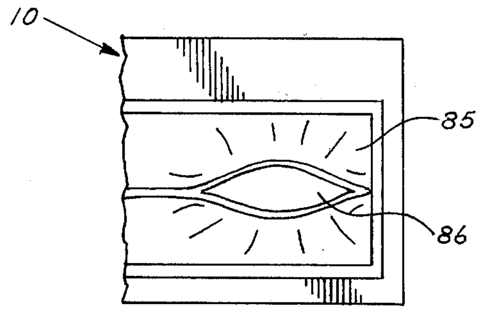
FIG. 12 is an end elevation view of a portion of the end cover member.

A cover member 85 for the access opening 86 is mounted at the end 15. Cover member 85 like cover member 77 is made of a dark, flexible fabric material and has two openings 86 defined by flexible bands into which the hands may be inserted to place them inside the housing through access opening 11. This member also is removably attached to the housing by a velcro-type strip 88 on the cover member 85 at the open end thereof as best seen in FIG. 11.

OPERATION

In the operation of the above-described apparatus, the plug 44 is usually plugged into an appropriate socket and a living organism such as a hand 19 shown or two hands is inserted into the access opening 18 with, for example, one or more of the fingers pressed against the underside of the viewing cell and specifically against layer 24.

Figure 5:
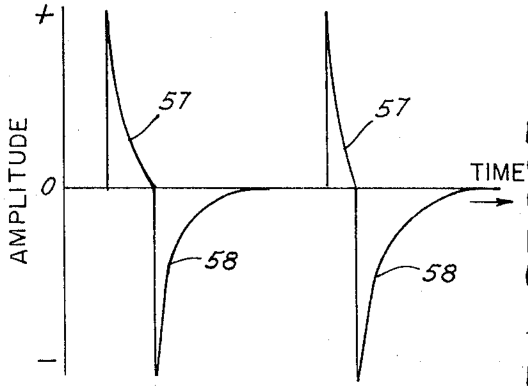
FIG. 5 is an approximate waveform for representing voltage and/or current at the output of the electric power source of FIG. 4.

Power switch SW2 and frequency switch SW1 are turned to an "on" position and the frequency potentiometer P or rheostat RH positioned at a desired setting. With the plug 44 plugged into an AC power supply, an electric voltage having a waveform characteristic like that shown in FIG. 5 is applied to the electrolyte 26 via conductor 27 and an electric field is produced between the electrolyte 26 and the portions of the fingers 22 placed against the dielectric layer 24 and a glow pattern results. The sequence of plugging in plug 44, insertion of the hands, and moving switches SW1 and SW2 can vary and is not critical.

Figure 6:
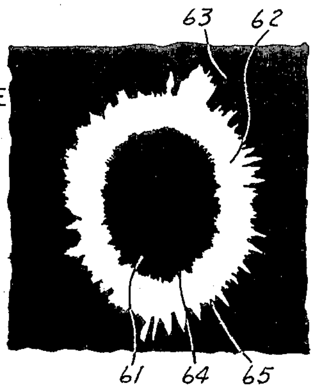
FIG. 6 is a top plan view of a representation of a glow pattern for the finger of a human body viewed during the operation of the viewing apparatus.
Figure 7:
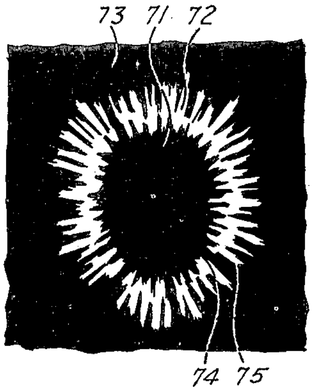
FIG. 7 is a top plan view of a representation of another glow pattern for the finger of a human body viewed during the operation of the viewing apparatus.
Figure 8:
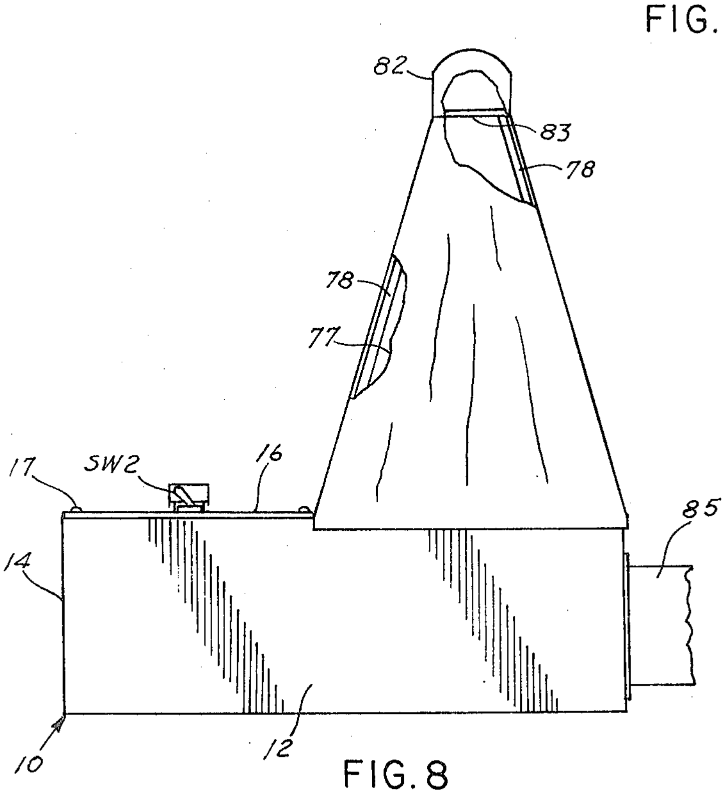
FIG. 8 is a side elevation view of the viewing apparatus of FIG. 1 with top and end cover members shown mounted thereon.

In FIGS. 6 and 7 there is shown for purposes of illustration, glow patterns representing a tip portion of a single finger area as it might be viewed looking down into the viewing cell 21. In FIG. 6 the image shown has a central dark area 61 corresponding to finger area 22 indicated in FIG. 2 that is a portion of the finger which is pressed on the inside dielectric layer 24. Around or encircling area 61 there is a glow band or halo 62 and then a darker outer area 63. The glow band or halo 62 has an inner periphery 64 and an outer periphery 65. The width and brightness of this glow band 62 varies greatly from organism to organism. These patterns have what is commonly referred to as a plurality of discharge channels radiating out from the organism. In the illustration shown in FIG. 7, there is an inner dark area 71, glow band 72, darker outer area 73 together with an inner periphery 74 and outer periphery 75. While the glow pattern of FIG. 6 is generally continuous throughout its circumferential extent, the glow pattern in FIG. 7 is broken and discontinuous. Variations or irregularities in the pattern occur at both the inside periphery and the outside periphery in the form of what is commonly referred to as flares, globules, sparks, dark blotches or broken dark areas, sporadic areas the the like.

The glow patterns illustrated in FIGS. 6 and 7 have a discharge channel that contains a potential glow configuration of a corresponding part of the electric field formed by some point of the organism and its electric or dielectric characteristics. In this way a discharge in the aggregate is a group of channels of various densities. It has been theorized that these channels carry the physical, chemical and dynamic characteristics of the organism transformed into electrical characteristics. It has further been theorized that by studying the geometric figures, their spectrum and the dynamics of development, it may be possible to judge the biological state of an organism and its organs including disease, health, mood and pathology.

Figure 13:
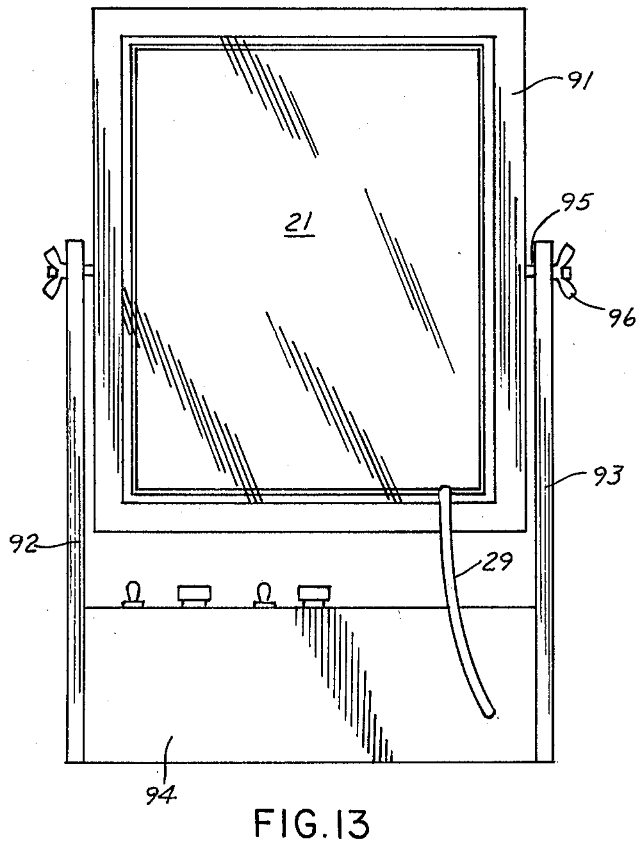
FIG. 13 is a side elevation view of another form of viewing apparatus.
Figure 14:
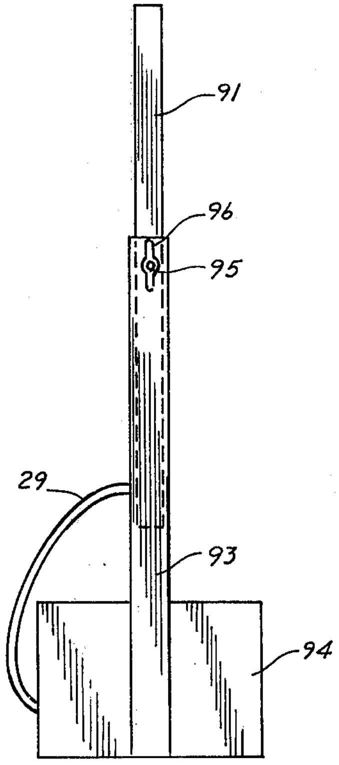
FIG. 14 is an end elevation of the viewing apparatus of FIG. 13.

Referring now to FIGS. 13 and 14, there is shown another form of viewing apparatus which comprises a viewing cell 21 which has the same construction shown in FIG. 3 above-described which is mounted in a frame 91 which is similar in construction to that of a picture frame supported in an upright position on uprights 92 and 93 mounted on the sides of a housing 94. The housing 94 contains the electric power supply circuits shown in FIG. 4 or the equivalent thereof with electric power being supplied to the viewing cell 21 via line 29. The frame 94 is pivotally mounted on the uprights by means of a pivot pin 95 associated with each upright and a wing nut threaded on the pin outside the upright. In this way the cell may be pivoted about a fixed axis between the upright position shown and a horizontal position for the viewing of a variety of living organisms including leaves, animals and the like. The operation thereof is similar to the other form shown and described with reference to the form shown in FIGS. 1 through 12.

Although the present invention has been described with a certain degree of particularity, it is understood that the present disclosure has been made by way of example and that changes in details of structure may be made without departing from the spirit thereof.

What is claimed is:

1. In a glow pattern viewing cell for observing glow patterns surrounding a living organism, the combination comprising:

at least one substantially transparent dielectric layer against which a living organism at a substantially ground potential is positioned; and a substantially transparent sheet of electrolyte on a face of said dielectric layer, said electrolyte having an electrically conductive interface means extending around and in electrical contact with a peripheral edge portion of said sheet of electrolyte for the distribution of electric energy through said sheet of electrolyte to which an oscillatory electric voltage is applied to produce an electric field between the electrolyte and the living organism through said dielectric layer whereby to produce a glow pattern about the living organism that is visible by looking through said dielectric layer and said electrolyte.

2. In a viewing cell as set forth in claim 1 wherein said electrolyte is in the form of a liquid.

3. In a glow pattern viewing cell as set forth in claim 1 wherein said electrolyte is a solution of salt water.

4. In a glow pattern viewing cell as set forth in claim 1 wherein said dielectric layer is a Plexiglas material.

5. In a glow pattern viewing cell as set forth in claim 1 wherein there are a pair of substantially transparent, outer dielectric layers that are separated by said electrolyte in a sandwich-type arrangement.

6. In a glow pattern viewing cell as set forth in claim 5 including means at the edges of said outer dielectric layers to seal the electrolyte between said outer dielectric layers.

7. In a glow pattern viewing cell as set forth in claim 5 including a spacing means made of a dielectric material disposed between said outer dielectric layers arranged along the edges of said outer dielectric layers, said spacing means being sealed to said dielectric layers by an adhesive and holding the pair of dielectric layers a preselected distance apart to form a closed volume therein for containing said electrolyte with said input means passing through said spacing means in a sealed relation thereto.

8. In a glow pattern viewing cell as set forth in claim 1 wherein said interface means includes a loop of electrically conductive wire in contact with the electrolyte and extending around the edges of the dielectric layer and the outer perimeter of said sheet of electrolyte, said conductive wire having adjacent end portions extending through and projecting from an edge of said sheet of electrolyte to a common terminal.

9. In a glow pattern viewing cell for observing glow patterns about a living organism, the combination comprising:

a pair of flat, substantially transparent, outer sheets of a dielectric material spaced apart from one another against which a living organism at substantially ground potential is positioned;

a substantially transparent sheet of electrolyte in a liquid form sandwiched between said outer sheets, there being a thin, narrow, rigid spacing strip of a dielectric material between said outer sheets at the edge thereof for holding the outer sheets a selected distance apart, said spacing strip being adhesively secured to the outer sheets to form a sealed volume for containing said electrolyte;

a loop of electrically conductive wire in the sealed volume in electrical contact with said electrolyte and extending around the edges of the outer sheets inside said spacing strip, said wire having end portions extending through an edge of said sheet of electrolyte to be connected to an electric activating voltage.

10. In a glow pattern viewing apparatus for observing glow patterns surrounding living organisms, the combination comprising:

a substantially transparent viewing cell having a pair of substantially transparent dielectric layers spaced apart from one another and a substantially transparent sheet of electrolyte in the form of a liquid sandwiched between said pair of dielectric layers;

an electrically conductive interface member extending around and in electrical contact with a peripheral edge portion of said sheet of electrolyte between said dielectric layers for the distribution of electric energy through said sheet of electrolyte; and electric power supply means for applying an oscillatory, electric energy to said interface member whereby an electric field is produced between said sheet of electrolyte and a living organism pressed against one of said dielectric layers to produce a glow pattern about the living organism placed on said one dielectric layer characterizing the condition of said living organism.

11. In a glow pattern viewing apparatus for observing glow patterns surrounding living organisms, the combination comprising:

a housing;

a viewing cell supported by the housing, said viewing cell having a pair of spaced layers of substantially transparent dielectric material separated by a sheet of electrolyte, said electrolyte having an electrically conductive interface member extending around and in electrical contact with a peripheral edge portion of said sheet of electrolyte between said dielectric layers for the distribution of electric energy through said sheet of electrolyte; and electric power supply means in said housing for applying an oscillatory, electric voltage to said interface member to activate said sheet of electrolyte to produce an electric field between one of said layers of dielectric material against which a living organism is positioned to produce a glow pattern about said living organism that is visible by looking through said viewing cell.

12. In a glow pattern viewing apparatus as set forth in claim 11 wherein said housing has upright means adapted to support said viewing cell for rotation about a fixed axis.

13. In a glow pattern viewing apparatus as set forth in claim 11 wherein said housing has a control panel for regulating said electric power supply means.

14. In a glow pattern viewing apparatus as set forth in claim 11 wherein said housing has a wall with a viewing opening into the housing and an access opening into the housing, said viewing cell being mounted inside said housing with one of said layers facing said viewing opening and the other of said layers adjacent said access opening.

15. In a glow pattern viewing apparatus as set forth in claim 14 wherein the living organism being viewed is positioned against a face of said cell by insertion through said second opening.

16. In a glow pattern viewing apparatus as set forth in claim 15 including a cover member for said viewing opening, said cover member having a flexible opaque portion with an open end removably fastened to the housing about said viewing opening for inhibiting light from the viewing cell and a viewing head with a lens through which the viewer looks to look through said viewing cell, said viewing head being conformable to the area about the eyes of the viewer.

17. In a glow pattern viewing apparatus as set forth in claim 16 wherein said opaque portion is a fabric material and a frame removable from the housing for supporting the cover member on said housing.

18. In a glow pattern viewing apparatus as set forth in claim 15 inclusive of a cover member for said access opening having a flexible opaque portion with an open end removably fastened to the housing about said access opening to inhibit light from the viewing cell, said opaque portion having at least one flexible access opening for inserting living organisms into the cover member and housing.

19. In a glow pattern viewing apparatus as set forth in claim 11 wherein said electric power supply means includes an oscillator circuit with a solid state switching device, an AC to DC voltage doubler circuit and an output circuit with a primary winding and a secondary winding inductively coupled to the primary winding for increasing voltage and decreasing current between said primary and secondary winding, the secondary winding being coupled to said input means, said output circuit having a capacitor controlled by a second solid state switching device, said capacitor being charged by said voltage doubler circuit, said oscillator circuit regulating the frequency of the charging and discharging of said capacitor.

20. In a glow pattern viewing apparatus for living organisms, the combination comprising:

a housing having a first wall with a viewing opening into the housing and a second wall adjacent the first wall with an access opening into the housing;

a viewing cell mounted in the housing and facing the viewing opening, said viewing cell having a pair of spaced layers of transparent dielectric material separated by a sheet of transparent electrolyte having electric input means connected thereto;

a first cover member having an open end removably fastened to said housing about said viewing opening for inhibiting light from said viewing cell, said first cover member having an opaque, flexible fabric portion with a viewing head at one end thereof through which the viewer looks and a frame to support said first cover member on the housing;

a second cover member having an open end removably fastened to said housing about said access opening for inhibiting light from the viewing cell, said second cover member having an opaque, flexible fabric portion with a pair of flexible access openings through which the hands of a user may be inserted to place portions of the hands against a face of the viewing cell; and an electric power supply means in said housing for applying an oscillatory, electric voltage to said input means to activate said electrolyte to produce an electric field between said electrolyte and one of said layers of dielectric material against which a living organism is positioned to produce a visible glow pattern about said living organism characterizing the condition of said living organism, said power supply means having a control portion on said housing including first control means for varying the frequency of the electric oscillations applied to the electrolyte layer, and second control means for varying the amplitude of the electric oscillations applied to the electrolyte.

21. In a glow pattern viewing apparatus as set forth in claim 20 wherein said first and second cover members are fastened to the housing by a strip of Velcro on the housing and on the associated opened end of each cover member.

* * * * *